(12) United States Patent
Nolde (10) Patent No.: US 8,021,364 B2
(45) Date of Patent: Sep. 20, 2011

(54) RASP ATTACHMENT FOR A MOTOR-DRIVEN SURGICAL HAND-HELD DEVICE

(75) Inventor: Martin Nolde, Dillingen (DE)

(73) Assignee: Martin Nolde, Dillingen (DE)

( * ) Notice: Subject to any disclaimer, the term of this patent is extended or adjusted under 35 U.S.C. 154(b) by 1186 days.

(21) Appl. No.: 11/248,107

(22) Filed: Oct. 11, 2005

(65) Prior Publication Data

US 2006/0089650 A1    Apr. 27, 2006

Related U.S. Application Data

(63) Continuation of application No. PCT/EP2004/001863, filed on Feb. 25, 2004.

(30) Foreign Application Priority Data

Apr. 11, 2003  (DE) ................................ 103 16 781
Apr. 11, 2003  (DE) .............................. 203 05 915 U (51) Int. Cl.
| A61B 17/00 | (2006.01) |
| B24B 5/00 | (2006.01) |
| B24B 7/00 | (2006.01) |
| B24B 23/00 | (2006.01) |
| B24B 27/08 | (2006.01) |

(52) U.S. Cl. ........................... 606/85; 451/162; 451/356

(58) Field of Classification Search ................ 606/79, 606/80, 84, 85; 451/162, 163, 356, 421, 451/526; 83/452, 612, 845; 30/274, 380
See application file for complete search history.

(56) References Cited

U.S. PATENT DOCUMENTS

| 3,914,906 | A | * | 10/1975 | Barnes ........................ 451/356 |
| 4,685,181 | A | * | 8/1987 | Schwartz ................. 407/29.13 |
| 4,954,231 | A | | 9/1990 | Correia et al. |
| 5,022,189 | A | * | 6/1991 | Saul ............................ 451/356 |
| 5,147,364 | A | * | 9/1992 | Comparetto ................. 606/85 |
| 5,725,530 | A | * | 3/1998 | Popken ........................ 606/82 |
| 5,725,531 | A | * | 3/1998 | Shapiro ......................... 606/85 |
| 5,759,093 | A | * | 6/1998 | Rodriguez .................. 451/356 |
| 5,814,049 | A | * | 9/1998 | Pratt et al. ..................... 606/80 |
| 5,836,764 | A | * | 11/1998 | Buchanan ................... 433/102 |
| 6,048,345 | A | | 4/2000 | Berke et al. |
| 6,478,805 | B1 | * | 11/2002 | Marino et al. .............. 606/170 |
| 6,733,496 | B2 | * | 5/2004 | Sharkey et al. ............... 606/41 |
| 7,018,381 | B2 | * | 3/2006 | Michael et al. .............. 606/80 |
| 7,390,330 | B2 | * | 6/2008 | Harp .......................... 606/171 |
| 2002/0022854 | A1 | | 2/2002 | Irion et al. |
| 2003/0225412 | A1 | * | 12/2003 | Shiraishi ....................... 606/85 |

FOREIGN PATENT DOCUMENTS

| DE | 4235278 | 10/1992 |
| DE | 19961027 | 12/1999 |
| EP | 03780002 | 7/1990 |

(Continued)

*Primary Examiner* — Thomas C Barrett
*Assistant Examiner* — David W Bates
(74) *Attorney, Agent, or Firm* — Michael A. Glenn; Glenn Patent Group (57) ABSTRACT

A rasp attachment for a motor-driven surgical hand-piece includes a mounting means for mounting the rasp attachment to the motor-driven surgical hand-piece and a rasp area which is implemented to take off material from a surface in a reciprocating movement of the rasp attachment caused by the motor-driven surgical hand-piece. the rasp to is curved and elastically deformable at least in the rasp area.

8 Claims, 5 Drawing Sheets

| | FOREIGN PATENT DOCUMENTS | |
|---|---|---|
| EP | 0634145 A | 7/1994 |
| EP | 0788773 A | 2/1997 |
| GB | 2271735 A | 4/1994 |
| JP | 2001-321360 A1 * | 10/2001 |
| WO | WO93/15665 A | 8/1993 |
| WO | WO 0108571 A1 * | 2/2001 |

* cited by examiner

FIG 6

RASP ATTACHMENT FOR A MOTOR-DRIVEN SURGICAL HAND-HELD DEVICE

CROSS-REFERENCE TO RELATED APPLICATIONS

This application is a continuation of co-pending International Application No. PCT/EP2004/001863, filed Feb. 25, 2004, which designated the United States and was not published in English.

BACKGROUND OF THE INVENTION

1. Field of the Invention

The present invention relates to a rasp attachment for a motor-driven hand-held device for taking off bones or other solid tissue.

2. Description of the Related Art

In numerous surgical operations bone substance is taken off by filing, rasping, planing or milling in order to model bone surfaces. This is, for example, required to remove a narrow pass situation, prepare the insertion of an implant or post-process surface structures which resulted from a previous coarser processing step. Subsequently, an example from shoulder surgery is described.

Figure 5:
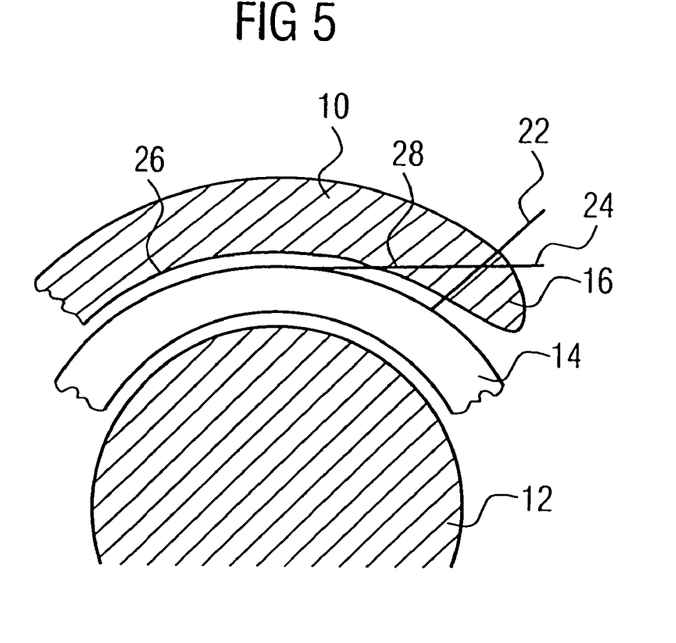
FIGS. 5 and 6 show diagrams of an operation area before or after acromioplastics, respectively.
Figure 6:
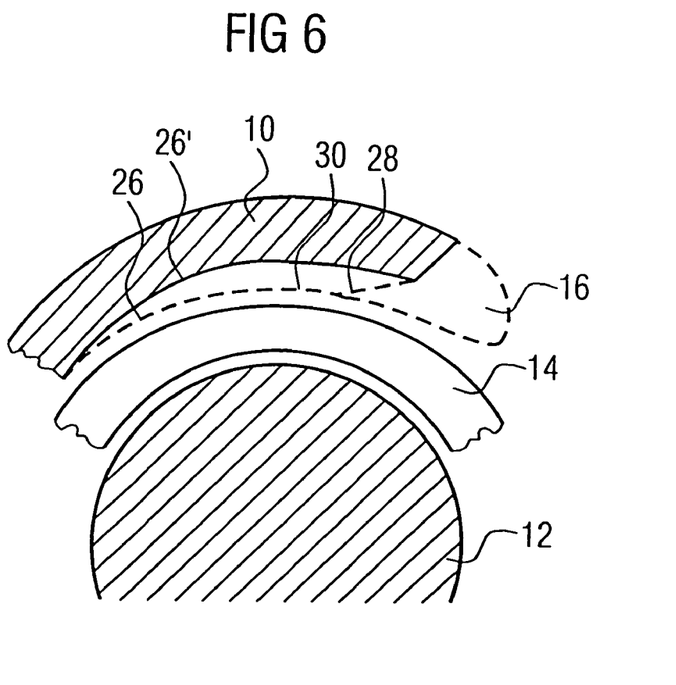

At the human shoulder, an anatomic variant of the akromion frequently leads to a bone narrow pass situation which is referred to as the impingement syndrome in the English-speaking world. This narrow pass situation mainly leads to chronic movement and stress-dependent pain in the shoulder area in the middle phase of life. Frequently, the chronic, mechanical irritation also leads to progressing damage of a tendon cuff located below the akromion, the rotator cuff. For treating the impingement syndrome the extension of the slip space below the akromion has been accepted worldwide. FIGS. 5 and 6 show schematic illustrations of the shoulder roof in the longitudinal section or sagittal section, respectively, in two different stages of treatment.

FIG. 5 shows the acromion 10, the humerus head 12 and the intermediate rotator cuff 14 in the original state. The outer rim 16 of the acromion 10 is drawn down too far, so that the movement of the shoulder joint or the humerus head 12, respectively, in the acromion is restricted. The subsequently illustrated surgical operation is referred to as acromioplastics.

In classical acromioplastics according to the specification of the first author (Neer) the acromion is changed using a chisel. In the last few years, an oscillating saw has mainly been used for the treatment of the acromion 10. By using the oscillating saw, two saw cuts 22, 24 are performed in order to remove the excessive rim 16 of the acromion 10. Using the saw, however, only straight or level saw cuts, respectively, may be generated. At the bottom side 26 of the acromion 10 facing the rotator cuff 14 or the humerus head 12, respectively, an edge 28 thus results at which generally a flash remains. This flash is subsequently removed using a hand-held rasp or a cherry. This process is tiring, however, and not very tissue-conserving.

Depending on the severity of the deviation of the shape of the acromion 10 from the ideal standard, in acromioplastics further the bottom face or bottom side 26, respectively, of the acromion is thinned in order to extend the slip space of the shoulder joint. The state of the acromion 10 after the acromi-noplastics is shown in FIG. 6. Dashed lines indicate the contour of the acromion 10 before the operation and before thinning. The edge 16 of the acromion 10 was removed by the sawing cuts 22, 24, and at the bottom side 26 of the acromion 10 a layer 30 was removed in order to form a new bottom side 26' of the acromion 10.

The state represented in FIG. 6 illustrates an ideal state. Generally, a concave shaping of the bottom face 26 of the acromion 10 may not be achieved using the hand-held rasp, however. A further disadvantage of the prior art is, as it was already indicated, that the use of a hand-held rasp or a cherry for processing the acromion 10 is tiring and not very tissue-conserving.

From U.S. Pat. No. 6,048,345 A a medical device in the form of a file for removing and forming solid body materials is known. A file-head which may comprise different shapes is connected to means for reciprocately moving the file-head via an arm portion.

From WO 93/15665 A a surgical instrument is known including drive means for reciprocating a cutting means comprising a rasp face.

EP 0788773 A1 discloses a tool for implanting an endoprosthesis in a cavity of a human bone. The tool contains a rasp body which corresponds to the prosthesis shank to be anchored in the bone cavity. At the proximal end of the rasp body a hand-grip is removably mounted.

EP 0634145 A1 discloses a hollow shank rasp for the preparation of a hollow bone for the reception of a stem-shaped endoprosthesis. Proximally a hand-grip may be attached to the hollow shank rasp.

SUMMARY OF THE INVENTION

It is the object of the present invention to provide an improved material take-off tool for surgical applications.

In accordance with one aspect, the present invention provides a rasp attachment for a motor-driven surgical hand-piece, having mounting means for mounting the rasp attachment to the motor-driven surgical hand-piece; and a rasp area which is implemented to take off material from a surface in a reciprocating movement of the rasp attachment caused by the motor-driven surgical hand-piece, wherein the rasp attachment is curved and elastically deformable, at least in the rasp area, wherein the elastic deformability of the rasp attachment in an area remote from the mounting means is higher than in an area close to the mounting means.

The present invention provides a rasp attachment for a motor-driven surgical hand-held device having a mounting means for mounting the rasp attachment to the motor-driven surgical hand-held device and a rasp area which is implemented to take off material from a surface in a reciprocating movement of the rasp attachment by the motor-driven surgical hand-held device. The rasp attachment is curved and elastically deformable at least in the rasp area, wherein the elastic deformability in an area remote from the mounting means (44) is higher than in an area close to the mounting means (44).

The present invention is based on the finding that a surgeon may respectively take off or model solid tissue, for example a bone, a lot more easily if he can, in this process, exclusively concentrate on the arrangement and alignment of the rasp in relation to the tissue to be modeled, to the contact pressure and feeling the interaction between the rasp and the tissue, and does not simultaneously have to apply force and energy and pay attention to the evenness of his manual rasp movements. The present invention has in this connection the advantage that the surgeon is able to take off material with less effort and considerably more sensitively, evenly and smoothly than when using a conventional hand rasp.

According to the present invention, the actual rasp operation is performed by the motor-driven surgical hand-held device, the intrinsic characteristic of which is that it performs the reciprocating material take-off movement of the rasp or filing attachment, respectively, almost completely uniformly in a cinematic and dynamic respect. The surgeon can concentrate on accurately determining the location of the material take-off by the arrangement and alignment of the rasp attachment in relation to the tissue to be modeled, setting the take-off rate by the contact pressure of the rasp attachment or from its rasp area to the surface to be removed, respectively, observing the interaction of the rasp attachment with the surface to be removed and shifting the location of the material take-off as continuously as possible if applicable by a slow and uniform swivel or translation movement of the hand-piece in order to, for example, prevent the formation of steps. The observation of the interaction of the rasp attachment with the surface to be treated mainly includes an observation of the friction force between the rasp area and the surface to be removed. Further, it includes an observation of the reaction on the motor-driven hand-piece which, for example, influences the frequency of the reciprocating movement or a noticeable shaking of the hand-piece. Apart from that, the surgeon may, for example, feel steps and edges on the surface to be removed, for example, via the rasp attachment and the hand-piece. All of this enables an easier, fatigue-reduced and thus more concentrated, precise, tissue-conserving, faster and thus more time-saving operation.

The rasp attachment is curved in one or two directions at least in the rasp area, wherein the rasp area may be both convex and concave. A curved rasp area has the advantage that curved surfaces may easily be modeled and that the risk of a step formation at a surface to be taken off is reduced and almost automatically continuous or rounded transitions, respectively, result.

Further, the rasp attachment is flexible at least in the rasp area, which enables an individual adjustment of the resection measure. In particular, an elasticity of the rasp attachment enables an adjustment of the shape of the same to the surface to be treated, merely by the force applied by the hand-piece to the rasp attachment in the direction towards the surface to be treated. The elasticity of the rasp attachment thus also contributes to the formation of step-free, rounded surfaces with transitions as continuous as possible and, for example, reliably prevents the formation of a flash.

Again preferably, the rasp attachment comprises a higher elasticity at its attachment or in an area remote from the hand-piece as compared to an area close to the hand-piece. This further improves the adaptation of the shape of the rasp attachment to the surface to be processed. An optimum adaptation or an optimum adaptability, respectively, of the rasp attachment to the surface to be treated is achieved when the elasticity of the rasp attachment is continuously increasingly more elastic from the mounting means to its end remote from the mounting means.

Preferably, the rasp attachment is further perforated at least in the rasp area in order to enable a passage of rinsing liquid. A uniform rinsing of the rasp area and the surface being processed is important in order to take away taken off material and so that the rasp does not clog but keeps its material take-off effect. Further, rinsing is important in order to respectively cool or regulate the temperature of the surface being treated and the surrounding tissue in order to prevent an excessive heating up which would cause damage to the tissue. Preferably, the rasp attachment is oblong, wherein the mounting means is arranged at one end and the rasp area at the other end of the rasp attachment. Further, the rasp attachment is preferably implemented such that it is reciprocately pivoted around an axis close to the mounting means by the motor-driven surgical hand-piece, so that the rasp area performs an oscillating movement along an arch segment. This enables a uniform and, depending on the amplitude of the oscillation, planar or also local take-off of material. A rasp area within the scope of the present invention is also a fine rasp area or filing area, respectively. Further, the term "rasp area" according to the present invention includes, apart from a filing area, also a milling area with one or several edges or blades, respectively, arranged perpendicularly to the direction of movement of the rasp area.

Preferred implementations are defined in the sub-claims.

BRIEF DESCRIPTION OF THE DRAWINGS

Preferred embodiments of the present invention are explained in more detail in the following with reference to the accompanying drawings, in which.

DESCRIPTION OF THE PREFERRED EMBODIMENTS

Figure 1A:
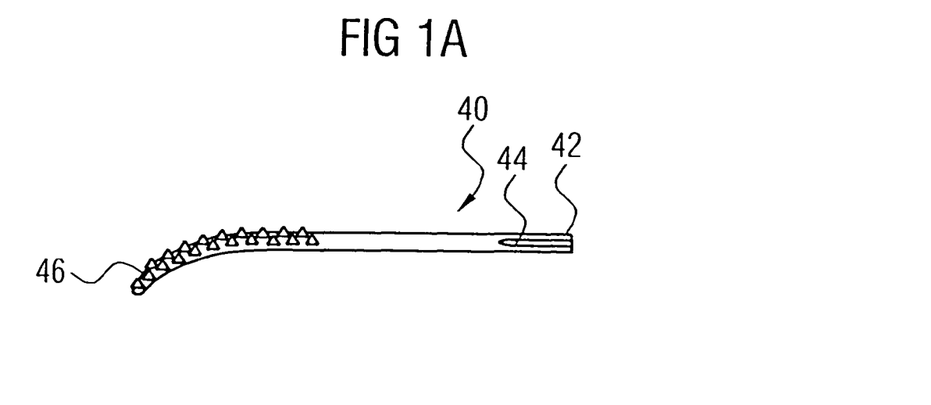
FIG. 1A to 1C show schematic views of a rasp attachment according a preferred embodiment of the present invention from three directions.
Figure 1B:
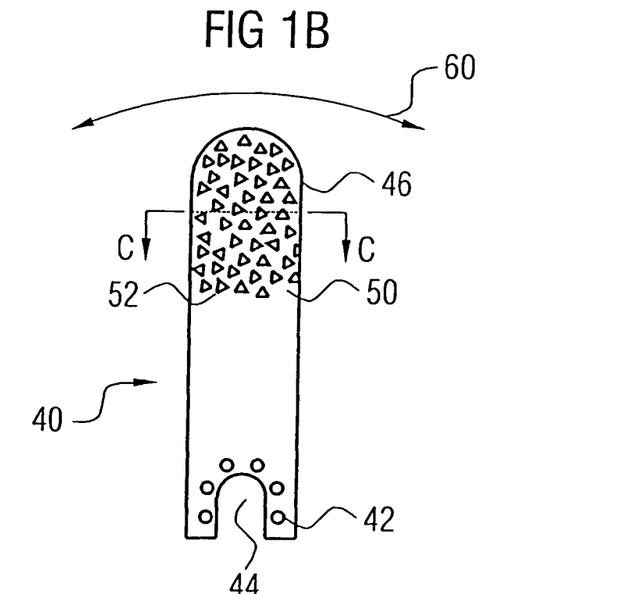
Figure 1C:
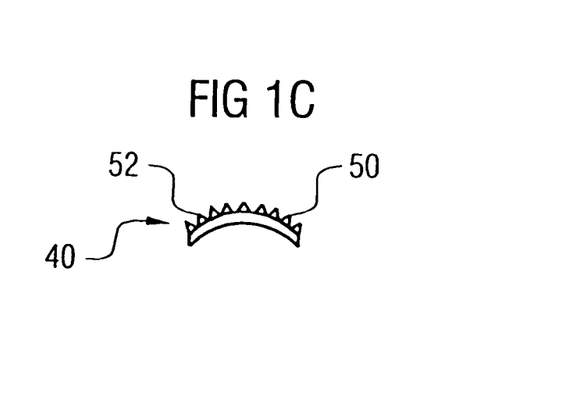

FIGS. 1A, 1B, 1C show a rasp attachment 40 according to a preferred embodiment of the present invention from three different perspectives. The rasp attachment 40 has approximately the shape of a slightly curved, oblong small plate or metal sheet strip, respectively. FIG. 1A shows the rasp attachment 40 in a side view or from a direction perpendicular to the direction in which the rasp attachment has its greatest extension, respectively, and approximately parallel to the direction in which the rasp attachment 40 has its second largest extension. FIG. 1B shows the rasp attachment 40 in a view from above, in a view from the side at which the rasp area is arranged, and in a view from a direction in which the rasp attachment has its smallest extension, respectively. FIG. 1C shows an illustration of a section through the rasp attachment 40 along the line C-C in FIG. 1B.

It may be seen that the rasp attachment 40 approximately comprises the shape of an oblong, rectangular sheet-metal strip, wherein at its one end 42 mounting means 44 for mounting the rasp attachment 40 to a motor-driven surgical hand-piece is arranged. The other end 46 of the rasp attachment 40 is rounded off. Close to the rounded end 46 a rasp area 50 is arranged in which from the surface of the rasp attachment 40 one or several, preferably a plurality of small cones, pyramids, lands or other convex elements 52 protrude. Each convex element 52 comprises one or several (preferably sharp) edges which are implemented such that the same, when they are engaged with a surface along which the rasp area 50 is moved, take off material from the same. The rasp area 50 is in this respect similar to the rasp area of a conventional hand rasp or hand file.

In FIG. 1A it may be seen that the rasp attachment 40, in particular in the area of the rasp area 50, comprises a longitudinal curvature. In FIG. 1C it may be seen that the rasp attachment 40 further comprises, at least in the area of the rasp area 50, also a curvature in the transverse direction. The rasp area 50 is in this embodiment arranged at the convex side of the curvature of the rasp attachment 40.

The rasp attachment 40 is implemented to be operated preferably on a motor-driven surgical hand-held device reciprocately pivoting the rasp attachment 40 around an axis located close to the mounting means 44. The arrow 60 in FIG. 1B indicates this oscillating pivoting movement.

Figure 2:
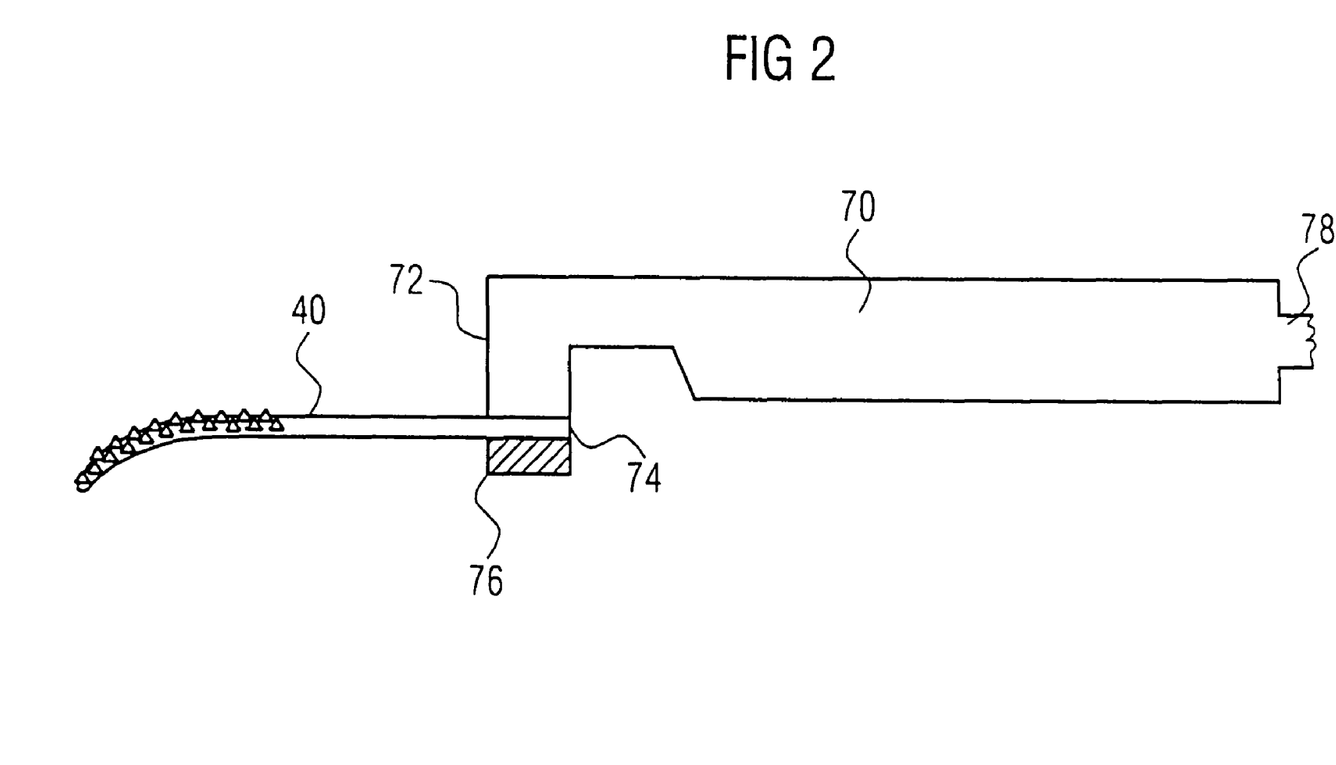
FIG. 2 shows a diagram of a rasp attachment according to the present invention comprising a motor-driven surgical hand-held device.

FIG. 2 is a schematic side view of the rasp attachment 40 illustrated in FIGS. 1A, 1B together with a motor-driven surgical hand-piece 70 to which the rasp attachment 40 is attached. The motor-driven surgical hand-piece 70 has an oblong ergonomically optimized shape facilitating a secure, non-positive (force-fit) and fatigue-free holding with one or two hands. At a front end 72, the motor-driven surgical hand-piece 70 comprises a receptacle 74 for receiving the mounting means 44 of the rasp attachment 40 facilitating a non-positive connection to the mounting means 44. A retaining element 76, for example a knurled screw, is provided and implemented to reliably hold the mounting means 44 of the rasp attachment 40 at the receptacle 74.

Via one or several tubes or a cable 78 the hand-piece 70 is provided with pressurized air or another fluid under pressure or with electrical power, respectively. A pneumatic or hydraulic or electric motor, respectively, driven in the interior of the motor-driven surgical hand-piece 70 turns the receptacle 74 to and fro. By this, the rasp area 50 of the rasp attachment 40, as illustrated in FIG. 1B by the arrow 60, is reciprocated along the shape of a circular arch. In other words, the rasp area 50 is reciprocated perpendicular to the longitudinal extension of the rasp attachment 40.

Alternatively, the hand-piece 70 is implemented so that it simultaneously causes, together with or also switchably instead of the reciprocating movement perpendicular to the longitudinal extension of the rasp attachment 40, a radial reciprocating movement of the rasp attachment. Here, a radial movement is a movement in parallel to the longitudinal extension of the rasp attachment 40. Both movements comprises, as far as they are performed simultaneously, equal or different amplitudes and frequencies.

Both, the motor-driven surgical hand-piece 70 and also the rasp attachment 40 may preferably be sterilized. Alternatively, the rasp attachment 40 is provided for a one-time use, after which it is discarded or disposed of, respectively.

Figure 3:
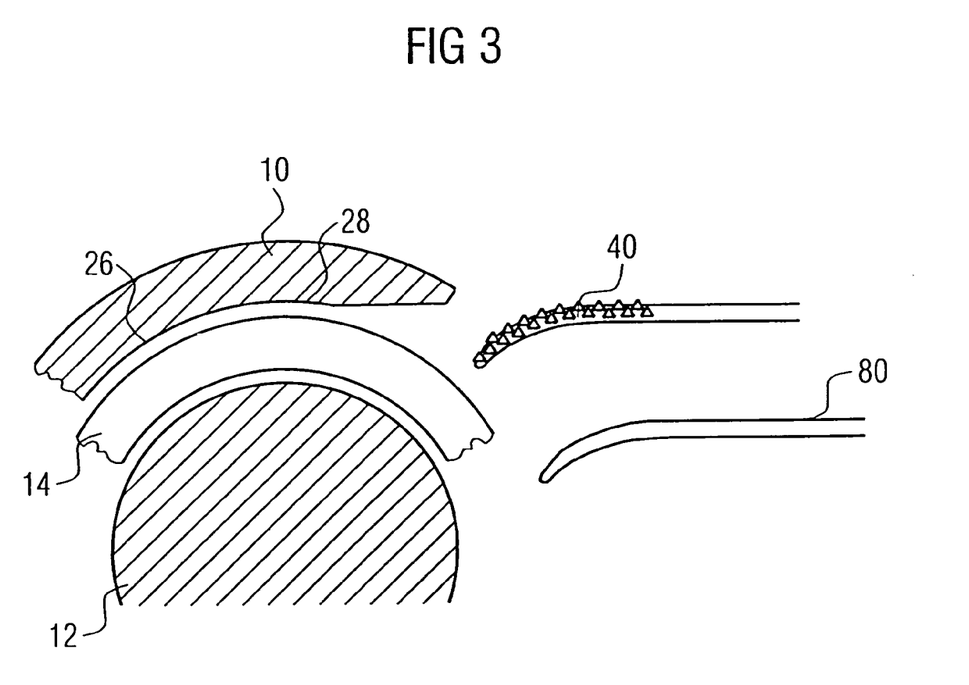
FIGS. 3 and 4 show diagrams of an operation area with a rasp attachment according to the present invention.
Figure 4:
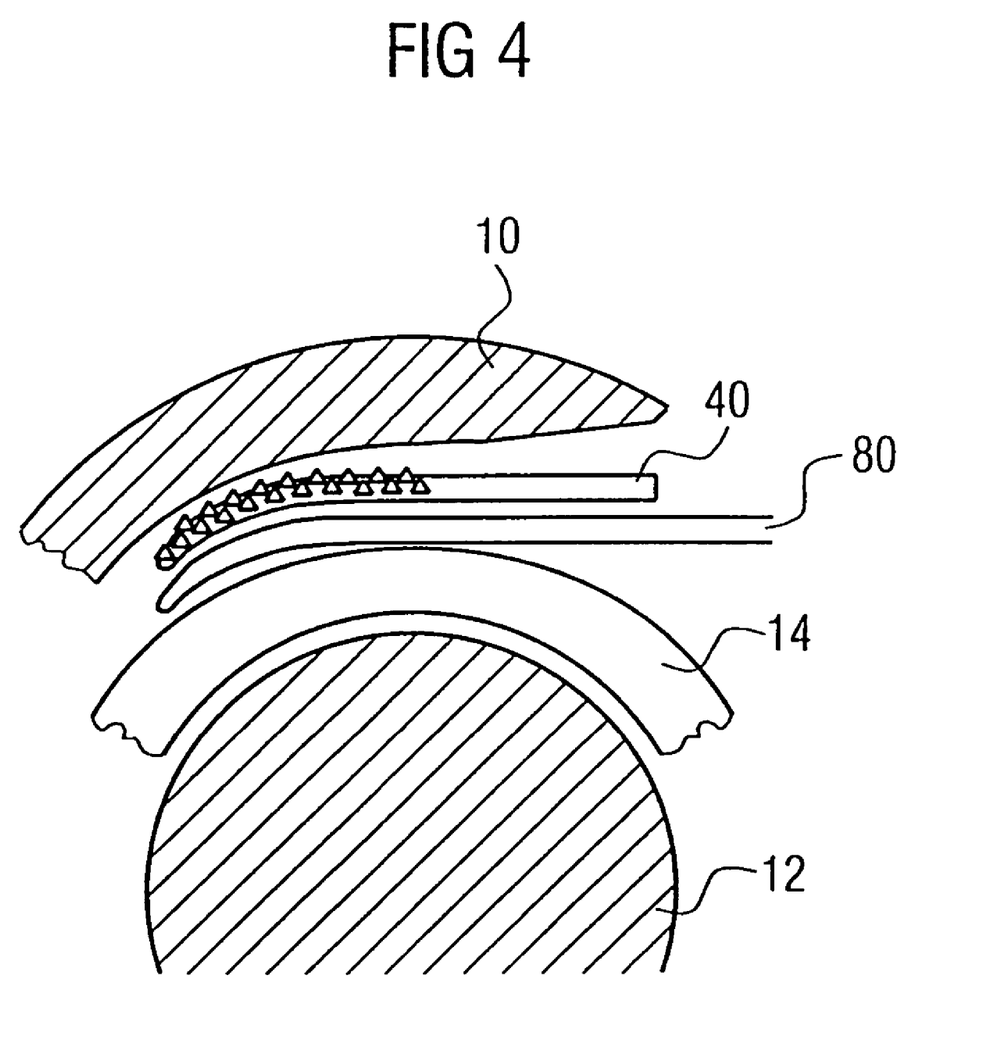

FIGS. 3 and 4 show schematic sectional views of an operation area and the use of the inventive rasp attachment. As an example, again the acromioplastics already described above is illustrated for treating the impingement syndrome. In FIG. 3, the acromion 10 is illustrated in the state after performing the two sawing steps already described above with reference to FIGS. 5 and 6. Initially, a flexible metal spatula (Dusseldorf spatula), as it is used in abdominal surgery, for the protection of the rotator cuff 14, is placed between the same and the acromion 10. By this spatula, the joint head or the humerus head 12, respectively, may be pressed down simultaneously with the rotator cuff 14 or moved away from the acromion 10, respectively. By this, additional operating space is provided between the rotator cuff 14 and the acromion 10. After placing the spatula 80, the rasp attachment 40 is inserted between the spatula 80 and the acromion 10. The thus obtained state is illustrated in FIG. 4. Now, by the oscillating movement of the rasp area 50 of the rasp attachment 40 along the bottom side 26 of the acromion 10 the same is taken off in order to achieve the state already illustrated above with reference to FIG. 6. By the use of the oscillating rasp attachment 40 with the curved rasp area 50 in one single operating step the bottom face 26 of the acromion is thinned, concavely shaped and the cutting surface of the preceding sawing cut is smoothed or the flash 28 is removed, respectively.

Apart from the above-described acromioplastics, the inventive rasp attachment may also be used in other operations in the orthopedic and traumatologic field in which bones or also other solid tissue is taken off or modeled, respectively. A further example for an application of the inventive rasp attachment is modern forefoot surgery, for which the rasp attachment and in particular the rasp area are to be designed correspondingly or the shape, size, curvature, elasticity and roughness of the rasp area 50 are to be optimized, respectively. For these and other surgical measures, the rasp surface or the rasp area, respectively, is either placed, as illustrated above with respect to the figures, at a convex surface or alternatively at a concave surface of the rasp attachment.

Further fields of use are oral surgery, hand surgery, neurosurgery and plastic and reconstructive surgery.

As already described above, a continuous rinsing of the operation area for cooling the same and for removing the resulting residue or the taken off material (for example bone meal and bone marrow cells) is important during the material take-off process or milling process, respectively. In order to favor rinsing the operation area and in particular a rinsing around the rasp attachment and its rasp area, the rasp attachment and in particular its rasp area is preferably provided with a perforation or with one or several holes, slots or openings of another type, respectively, which enable a passage of rinsing liquid from one side of the rasp attachment to its other side. The convex elements 52 and the openings may, for example, be formed by the fact that U-shaped or V-shaped sections are punched, milled or etched into a metal sheet forming the rasp attachment 40 and that the triangular, rectangular or semicircular sections of the metal sheet remaining within the sections are bent upwards.

The mounting area of the inventive rasp attachment is preferably designed according to the international standards for mountings of surgical instruments to hand-driven or motor-driven hand-pieces.

As mentioned above, the inventive rasp attachment is preferably elastic. Again preferably, the elasticity of the rasp attachment increases from the mounting means to the end facing away from the mounting means in order to achieve a good adaptation of the rasp attachment to the shape of the surface to be processed. Preferably, the elasticity is higher in a front third or a third remote from the mounting means, respectively, than in a back section or a section arranged close to the mounting means, respectively. An ideal adaptation or adaptability, respectively, is achieved in a continuous increase of the elasticity from the mounting means to the end facing away from the mounting means.

The greater the elasticity of the rasp attachment, the greater its adaptability and the better the same may also adapt to small surface irregularities. The lower the elasticity of the rasp attachment, the more force or pressure may be applied by the rasp attachment to the surface to be processed and the smoother the surface may be processed. Because of this, for every field of application and for every field of operation, respectively, a trade-off between elasticity and rigidity has to be found. The respectively selected elasticity of the inventive rasp attachment is here further dependent on the preferred operating technique of the surgeon.

While this invention has been described in terms of several preferred embodiments, there are alterations, permutations, and equivalents which fall within the scope of this invention. It should also be noted that there are many alternative ways of implementing the methods and compositions of the present invention. It is therefore intended that the following appended claims be interpreted as including all such alterations, permutations, and equivalents as fall within the true spirit and scope of the present invention.

What is claimed is:

1. A rasp attachment for a motor-driven surgical hand-piece, comprising:
   a substantially axial member comprising a first terminal end and a second terminal end wherein the substantial axial member is configured with decreasing thickness in the direction from the first terminal end towards the second terminal end;
   a mounting on the first terminal end for mounting the rasp attachment to the motor-driven surgical hand-piece, wherein the rasp attachment is configured such that, during rasp operation the second terminal end is a free end; and
   an integral rasp area on the second terminal end which is implemented to take off material from a surface in a reciprocating movement of the rasp attachment caused by the motor-driven surgical hand-piece, wherein the rasp attachment is curved and at least partially elastically deformable in the rasp area such that the rasp area may be deformed to a given shape, and wherein the rasp area is sufficiently rigid to maintain its given shape when driven over bone substance by a motor-driven surgical hand-piece,
   wherein the substantially axial member comprises at least one region having a elasticity higher than the elasticity in at least one other region due to the decreased thickness wherein the integral rasp area is located in the region having a higher elasticity than the other region and
   wherein the second terminal end and the integral rasp area are convex in a transverse direction with respect to a longitudinal extension of the rasp attachment.

2. The rasp attachment according to claim 1, having an oblong shape, wherein the mounting is arranged at an end of the rasp attachment and the rasp area is arranged at the opposite end of the rasp attachment.

3. The rasp attachment according to claim 2, which is implemented to take off material from the surface in a movement of the rasp area in the shape of a circular arch segment.

4. The rasp attachment according to claim 2, wherein the rasp area is further implemented to take off material from the surface in a longitudinal direction with a movement of the rasp attachment.

5. The rasp attachment according to claim 1, further comprising an opening facilitating a passage of a rinsing liquid through the rasp attachment.

6. The rasp attachment according to claim 1, wherein the mounting corresponds to an international standard for surgical devices.

7. A motor-driven surgical hand-piece comprising a rasp attachment for a motor-driven surgical hand-piece, comprising:
   a substantially axial member comprising a first terminal end and a second terminal end wherein the substantially axial member is configured with decreasing thickness in the direction from the first terminal end towards the second terminal end;
   a mounting on the first terminal end for mounting the rasp attachment to the motor-driven surgical hand-piece, wherein the rasp attachment is configured such that, during rasp operation the second terminal end is a free end; and
   an integral, rasp area on the second terminal end which is implemented to take off material from a surface in a reciprocating movement of the rasp attachment caused by the motor-driven surgical hand-piece, wherein the rasp attachment is curved and at least partially elastically deformable in the rasp area such that the rasp area may be deformed to a given shape, and wherein the rasp area is sufficiently rigid to maintain its given shape when driven over bone substance by a motor-driven surgical hand-piece,
   wherein the substantially axial member comprises at least one region having a elasticity higher than the elasticity in at least one other region due to the decreased thickness, wherein the integral rasp area is located in the region having a higher elasticity than the other region, and
   wherein the second terminal end and the integral rasp area are convex in a transverse direction with respect to a longitudinal extension of the rasp attachment,
   wherein an end of the rasp attachment remote from the mounting is, during rasp operation, a free end when the rasp attachment is mounted to the motor-driven surgical hand-piece.

8. A motor-driven surgical hand-piece comprising a rasp attachment according to claim 7, wherein the motor-driven surgical hand-piece is configured to reciprocately pivot the rasp attachment.

* * * * *